(12) United States Patent
Brück et al.

(10) Patent No.: US 6,576,661 B1
(45) Date of Patent: Jun. 10, 2003

(54) ACTIVE INGREDIENT COMBINATION HAVING INSECTICIDAL AND ACARICIDAL CHARACTERISTICS

(75) Inventors: Ernst Brück, Bergisch Gladbach (DE); Christoph Erdelen, Leichlingen (DE); Reiner Fischer, Monheim (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/129,589

(22) PCT Filed: Oct. 27, 2000

(86) PCT No.: PCT/EP00/10620
§ 371 (c)(1),
(2), (4) Date: May 7, 2002

(87) PCT Pub. No.: WO01/33966
PCT Pub. Date: May 17, 2001

(30) Foreign Application Priority Data

Nov. 9, 1999 (DE) .......................... 199 53 775

(51) Int. Cl.[7] ...................... A61K 31/335; A61K 31/34; A01N 33/12
(52) U.S. Cl. ...................................... 514/462
(58) Field of Search ........................ 514/462

(56) References Cited

U.S. PATENT DOCUMENTS

| | | | |
|---|---|---|---|
| 2,494,283 A | 1/1950 | Cassaday et al. | 260/461 |
| 2,502,258 A | 3/1950 | Hay et al. | 260/648 |
| 2,578,652 A | 12/1951 | Cassaday | 260/461 |
| 2,586,655 A | 2/1952 | Hook et al. | 260/461 |
| 2,685,552 A | 8/1954 | Stiles | 167/22 |
| 2,701,225 A | 2/1955 | Lorenz | 167/22 |
| 2,754,243 A | 7/1956 | Gysin et al. | 167/33 |
| 2,758,115 A | 8/1956 | Lorenz | 260/248 |
| 2,767,194 A | 10/1956 | Fancher | 260/326 |
| 2,812,280 A | 11/1957 | Wison et al | 167/30 |
| 2,812,281 A | 11/1957 | Meltzer et al. | 167/30 |
| 2,873,228 A | 2/1959 | Williard et al. | 167/22 |
| 2,903,478 A | 9/1959 | Lambrech | 260/479 |
| 2,908,605 A | 10/1959 | Beriger et al. | 167/22 |
| 2,956,073 A | 10/1960 | Whetstone et al. | 260/461 |
| 3,244,586 A | 4/1966 | Rigternik | 167/33 |
| 3,264,177 A | 8/1966 | Kenaga | 167/30 |
| 3,272,854 A | 9/1966 | Covey et al. | 260/456 |
| 3,309,266 A | 3/1967 | Magee | 167/22 |
| 3,530,220 A | 9/1970 | Buchanan | 424/320 |
| 3,591,662 A | 7/1971 | Lorenz et al. | 260/940 |
| 3,632,694 A | 1/1972 | Pearson et al. | 260/969 |
| 3,639,620 A | 2/1972 | Donninger et al. | 424/304 |
| 3,689,648 A | 9/1972 | Lorenz et al. | 424/210 |
| 3,711,477 A | 1/1973 | Schelling et al. | 260/247.1 |
| 3,716,600 A | 2/1973 | Magee | 260/959 |
| 3,729,565 A | 4/1973 | Harrison et al. | 424/326 |
| 3,748,356 A | 7/1973 | Wellinga et al. | 260/553 E |
| 3,759,941 A | 9/1973 | Sampei et al. | 260/307 H |
| 3,763,143 A | 10/1973 | Buchanan | 260/239 E |
| 3,781,355 A | 12/1973 | Harrison et al. | 260/564 R |
| 3,784,696 A | 1/1974 | Gubler | 424/308 |
| 3,801,680 A | 4/1974 | Magee | 260/950 |
| 3,825,634 A | 7/1974 | Magee | 260/956 |
| 3,825,636 A | 7/1974 | Kishino et al. | 260/964 |

(List continued on next page.)

FOREIGN PATENT DOCUMENTS

| | | |
|---|---|---|
| DE | 2753426 | 6/1978 |
| DE | 161 047 | 9/1984 |
| DE | 199 393 95 | 4/2000 |
| DE | 199 131 74 | 9/2000 |
| EP | 0 528 156 | 2/1993 |
| EP | 0 639 559 | 10/1997 |
| GB | 775085 | 9/1952 |
| GB | 834815 | 5/1960 |
| GB | 1 181 657 | 2/1970 |
| GB | 1 589 259 | 5/1981 |

OTHER PUBLICATIONS

Weeds 15, (month unavailable) 1967, pp. 20–22, Calculating Synergistic and Antagonistic Responses of Herbicide Combinations by S.R. Colby.

The Pesticide Manual, Eleventh Edition, Editor: C D S Tomlin, (Date Unavailable) Verticillium lecanii Biological Agent pp. 1266–1267.

The Pesticide Manual, Eleventh Edition, Editor: C.D.S. Tomlin (Date Unavailable) Azadirachtin Insecticide pp. 59–60.

The Pesticide Manual, Eleventh Edition, Editor: C.D.S. Tomlin (Date Unavailable) Trichogramma spp. Biological Agent pp. 1236–1237.

The Pesticide Manual, Eleventh Edition, Editor C.D.S. Tomlin (Date Unavailable) Milbemectin Acaricide, insecticide pp. 846–847.

** C Tomlin (ED): "The Presticide Manual, Tenth Edition" Pesticide Manual, GB, Farnham,.

BCPC, vol. Ed. 10, Page(s) 1335–1341 XP002099499 ISBN:0–948404–79–5 the index of the active agent classes.

Primary Examiner—Alton N Pryor
(74) Attorney, Agent, or Firm—Richard E.L. Henderson; Joseph C. Gil

(57) ABSTRACT

The present invention provides combinations of cyclic ketoenols of the formula (I)

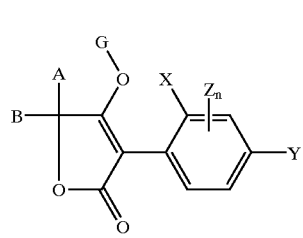

(I)

and the active compounds listed herein. The combinations have very good insecticidal and acaricidal properties.

3 Claims, No Drawings

U.S. PATENT DOCUMENTS

| | | | |
|---|---|---|---|
| 3,835,176 A | 9/1974 | Matsuo et al. | 260/465 D |
| 3,845,172 A | 10/1974 | Magee | 260/956 |
| 3,868,449 A | 2/1975 | Magee | 424/217 |
| 3,884,968 A | 5/1975 | Harrison et al. | 260/501.14 |
| 3,885,032 A | 5/1975 | Magee | 424/212 |
| 3,898,334 A | 8/1975 | Kishino et al. | 424/225 |
| 3,914,417 A | 10/1975 | Magee | 424/219 |
| 3,922,281 A | 11/1975 | Sauli | 260/307 C |
| 3,922,533 A | 11/1975 | Royal | 235/150.27 |
| 3,933,908 A | 1/1976 | Wellinga et al. | 260/553 E |
| 3,947,529 A | 3/1976 | Kishino et al. | 260/940 |
| 3,989,842 A | 11/1976 | Wellinga et al. | 424/322 |
| 3,996,244 A | 12/1976 | Fujimoto et al. | 260/332.2 A |
| 4,004,031 A | 1/1977 | Drabek | 424/327 |
| 4,013,717 A | 3/1977 | Wellinga et al. | 260/553 E |
| 4,013,793 A | 3/1977 | Kishino et al. | 424/210 |
| 4,016,179 A | 4/1977 | Fujimoto et al. | 260/347.5 |
| 4,024,163 A | 5/1977 | Elliott et al. | 260/347.4 |
| 4,031,235 A | 6/1977 | Fujimoto et al. | 424/274 |
| 4,035,378 A | 7/1977 | Staubli et al. | 260/302 E |
| 4,039,680 A | 8/1977 | Fujimoto et al. | 424/275 |
| 4,049,679 A | 9/1977 | Magee | 260/402.5 |
| 4,053,634 A | 10/1977 | Bellina et al. | 424/312 |
| 4,055,661 A | 10/1977 | Bellina et al. | 424/311 |
| 4,058,622 A | 11/1977 | Fujimoto et al. | 424/308 |
| 4,062,968 A | 12/1977 | Fujimoto et al. | 424/275 |
| 4,082,848 A | 4/1978 | Bellina et al. | 424/273 R |
| 4,097,581 A | 6/1978 | Farooq et al. | 424/278 |
| 4,110,443 A | 8/1978 | Magee | 424/212 |
| 4,110,469 A | 8/1978 | Wellinga et al. | 424/304 |
| 4,115,584 A | 9/1978 | Bellina et al. | 424/301 |
| 4,125,139 A | 11/1978 | Guertin et al. | 141/206 |
| 4,139,636 A | 2/1979 | Sirrenberg et al. | 424/322 |
| 4,143,157 A | 3/1979 | Bellina et al. | 424/314 |
| 4,148,918 A | 4/1979 | Bellina et al. | 424/314 |
| 4,159,328 A | 6/1979 | Ikeda et al. | 424/246 |
| 4,166,124 A | 8/1979 | Wellinga et al. | 424/273 R |
| 4,174,405 A | 11/1979 | Relyea et al. | 424/275 |
| 4,178,460 A | 12/1979 | Berkelhammer et al. | 562/426 |
| 4,179,575 A | 12/1979 | Martel et al. | 562/506 |
| 4,183,948 A | 1/1980 | Huff | 424/304 |
| 4,199,569 A | 4/1980 | Chabala et al. | 424/180 |
| 4,199,595 A | 4/1980 | Berkelhammer et al. | 424/304 |
| 4,215,139 A | 7/1980 | Fischer et al. | 424/300 |
| 4,224,227 A | 9/1980 | Martel et al. | 260/347.4 |
| 4,225,598 A | 9/1980 | Brechbuhler et al. | 424/249 |
| 4,231,932 A | 11/1980 | Martel et al. | 260/326 A |
| 4,239,777 A | 12/1980 | Berkelhammer et al. | 424/304 |
| 4,254,050 A | 3/1981 | Baum | 260/465 D |
| 4,254,051 A | 3/1981 | Baum | 260/465 D |
| 4,254,052 A | 3/1981 | Baum | 260/465 D |
| 4,257,978 A | 3/1981 | Martel et al. | 260/544 L |
| 4,260,633 A | 4/1981 | Anderson et al. | 424/304 |
| 4,266,074 A | 5/1981 | Fujimoto et al. | 560/105 |
| 4,279,835 A | 7/1981 | Martel et al. | 260/465 D |
| 4,310,542 A | 1/1982 | Martel et al. | 424/304 |
| 4,322,534 A | 3/1982 | Baum | 546/300 |
| 4,322,535 A | 3/1982 | Baum | 546/300 |
| 4,323,685 A | 4/1982 | Baum | 546/300 |
| 4,330,675 A | 5/1982 | Huff | 560/124 |
| 4,378,316 A | 3/1983 | Huff | 260/408 |
| 4,397,864 A | 8/1983 | Nakatani et al. | 424/282 |
| 4,409,150 A | 10/1983 | Wood | 260/465 D |
| 4,427,663 A | 1/1984 | Mrozik | 424/180 |
| 4,431,814 A | 2/1984 | Iwataki et al. | 548/230 |
| 4,442,116 A | 4/1984 | Iwataki et al. | 424/270 |
| 4,457,943 A | 7/1984 | Becher et al. | 424/322 |
| 4,503,071 A | 3/1985 | Hirano et al. | 514/521 |
| 4,510,098 A | 4/1985 | Crosby | 260/465 D |
| 4,510,160 A | 4/1985 | Robson | 514/521 |
| 4,511,350 A | 4/1985 | Romanauskas | 494/82 |
| 4,531,002 A | 7/1985 | Harris | 544/54 |
| 4,531,008 A | 7/1985 | Fujimoto et al. | 549/447 |
| 4,570,005 A | 2/1986 | Nakatani et al. | 549/435 |
| 4,590,272 A | 5/1986 | Shiokawa et al. | 544/335 |
| 4,606,862 A | 8/1986 | Harris | 260/402.5 |
| 4,607,044 A | 8/1986 | Wellinga et al. | 514/383 |
| 4,622,337 A | 11/1986 | Elliott et al. | 514/461 |
| 4,622,340 A | 11/1986 | Becher et al. | 514/594 |
| 4,666,894 A | 5/1987 | Maurer et al. | 514/86 |
| 4,687,845 A | 8/1987 | Hollowood et al. | 544/54 |
| 4,690,947 A | 9/1987 | Zeck et al. | 514/521 |
| 4,732,903 A | 3/1988 | Martel et al. | 514/345 |
| 4,742,072 A | 5/1988 | Jacobson et al. | 514/384 |
| 4,751,225 A | 6/1988 | Nishida et al. | 514/277 |
| 4,782,174 A | 11/1988 | Fuchs et al. | 558/354 |
| 4,798,837 A | 1/1989 | Drabek et al. | 514/594 |
| 4,833,151 A | 5/1989 | Wellinga et al. | 514/344 |
| 4,843,068 A | 6/1989 | Hamaguchi et al. | 514/63 |
| 4,845,097 A | 7/1989 | Matsumoto et al. | 514/234.2 |
| 4,879,292 A | 11/1989 | Nishida et al. | 514/241 |
| 4,883,806 A | 11/1989 | Martel et al. | 514/417 |
| 4,918,086 A | 4/1990 | Gsell | 514/351 |
| 4,918,088 A | 4/1990 | Gsell | 514/357 |
| 4,920,135 A | 4/1990 | Wellinga et al. | 514/344 |
| 4,931,439 A | 6/1990 | Kristinsson | 514/242 |
| 4,948,798 A | 8/1990 | Gsell | 514/275 |
| 4,950,668 A | 8/1990 | Okada et al. | 514/232.2 |
| 4,962,126 A | 10/1990 | Drabek | 514/587 |
| 4,963,572 A | 10/1990 | Gsell | 514/357 |
| 4,963,574 A | 10/1990 | Bachmann et al. | 514/357 |
| 4,970,222 A | 11/1990 | Nishida et al. | 514/369 |
| 4,970,330 A | 11/1990 | Huff | 558/407 |
| 4,980,506 A | 12/1990 | Drabek et al. | 564/442 |
| 4,996,325 A | 2/1991 | Kristinsson | 548/132 |
| 5,004,822 A | 4/1991 | Elliott et al. | 556/115 |
| 5,010,098 A | 4/1991 | Brown et al. | 514/426 |
| 5,034,404 A | 7/1991 | Uneme et al. | 514/365 |
| 5,049,571 A | 9/1991 | Gsell | 514/345 |
| 5,063,236 A | 11/1991 | Gsell | 514/318 |
| 5,107,017 A | 4/1992 | Drabek et al. | 560/358 |
| 5,110,986 A | 5/1992 | Kelly | 564/149 |
| 5,142,064 A | 8/1992 | Wellinga et al. | 549/404 |
| 5,153,224 A | 10/1992 | Drabek et al. | 574/594 |
| 5,175,301 A | 12/1992 | Minamida et al. | 546/272 |
| 5,192,778 A | 3/1993 | Kodaka et al. | 514/341 |
| 5,214,152 A | 5/1993 | Minamida et al. | 548/181 |
| 5,232,940 A | 8/1993 | Hatton et al. | 514/407 |
| 5,245,071 A | 9/1993 | Wellinga et al. | 560/27 |
| 5,256,679 A | 10/1993 | Minamida et al. | 514/357 |
| 5,262,383 A | 11/1993 | Fischer et al. | 504/195 |
| 5,264,584 A | 11/1993 | Kodaka et al. | 548/332.5 |
| 5,310,938 A | 5/1994 | Brown et al. | 548/557 |
| 5,319,092 A | 6/1994 | Jacobson et al. | 548/264.4 |
| 5,342,958 A | 8/1994 | Wellinga et al. | 548/317.5 |
| 5,367,093 A | 11/1994 | Dekeyser et al. | 560/27 |
| 5,411,963 A | 5/1995 | Dreikorn et al. | 514/259 |
| 5,434,181 A | 7/1995 | Kodaka et al. | 514/471 |
| 5,438,123 A | 8/1995 | Dekeyser et al. | 534/885 |
| 5,455,263 A | 10/1995 | Doscher et al. | 514/422 |
| 5,462,938 A | 10/1995 | Annus et al. | 514/229.8 |
| 5,470,984 A | 11/1995 | Jacobson et al. | 548/264.4 |
| 5,478,855 A | 12/1995 | Suzuki et al. | 514/374 |
| 5,489,603 A | 2/1996 | Uneme et al. | 514/365 |
| 5,532,365 A | 7/1996 | Kodaka et al. | 544/212 |
| 5,536,746 A | 7/1996 | Dekeyser et al. | 514/468 |
| 5,547,974 A | 8/1996 | Hatton et al. | 514/406 |
| 5,595,915 A | 1/1997 | Geysen | 436/518 |
| 5,608,077 A | 3/1997 | Hatton et al. | 548/365.1 |
| 5,614,527 A | 3/1997 | Kinoshita et al. | 514/256 |

| | | | | | | |
|---|---|---|---|---|---|---|
| 5,633,375 A | 5/1997 | Uneme et al. ............... 544/336 | | 5,852,012 A | 12/1998 | Maienfisch et al. ...... 514/229.2 |
| 5,696,256 A | 12/1997 | Kando et al. ............... 540/463 | | 5,916,618 A | 6/1999 | Hatton et al. ................ 426/532 |
| 5,708,170 A | 1/1998 | Annis et al. ................. 544/212 | | 6,022,871 A | 2/2000 | Maienfisch et al. ...... 514/229.2 |
| 5,714,191 A | 2/1998 | Hatton et al. ............... 426/532 | | 6,022,967 A | 2/2000 | Shiokawa et al. ........... 544/298 |
| 5,849,768 A | 12/1998 | Minamida et al. .......... 514/357 | | 6,124,297 A | 9/2000 | Minamida et al. ........... 514/255 |

ACTIVE INGREDIENT COMBINATION HAVING INSECTICIDAL AND ACARICIDAL CHARACTERISTICS

FIELD OF THE INVENTION

The present invention relates to new active compound combinations composed of known cyclic ketoenols on the one hand and of other known insecticidal active compounds on the other hand and which are highly suitable for controlling animal pests such as insects and undesired acarids.

BACKGROUND OF THE INVENTION

The fact that certain cyclic ketoenols have insecticidal and acaricidal properties has already been disclosed (EP-A-528 156). While the activity of these substances is good, it leaves something to be desired in some cases when applied at low rates.

DETAILED DESCRIPTION OF THE INVENTION

Furthermore, the fact that a large number of heterocycles, organotin compounds, benzoylureas and pyrethroids have insecticidal and acaricidal properties has already been disclosed (cf. WO 93-22 297, WO 93-10 083, DE-A 2 641 343, EP-A-347 488, EP-A-210 487, U.S. Pat. No. 3,264,177 and EP-A-234 045). Again, the action of these substances is not always satisfactory when applied at low rates.

It has now been found that compounds of the formula (I)

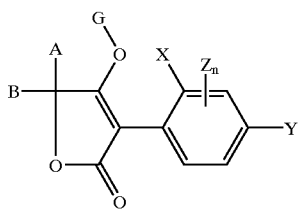

(I)

in which

X represents $C_1-C_6$-alkyl, halogen, $C_1-C_6$-alkoxy or $C_1-C_3$-halogenoalkyl, Y represents hydrogen, $C_1-C_6$-alkyl, halogen, $C_1-C_6$-alkoxy or $C_1-C_3$-halogenoalkyl, Z represents $C_1-C_6$-alkyl, halogen or $C_1-C_6$-alkoxy, n represents an integer from 0–3, A and B are identical or different and represent hydrogen or optionally halogen-substituted straight-chain or branched $C_1-C_{12}$-alkyl, $C_3-C_8$-alkenyl, $C_3-C_8$-alkinyl, $C_1-C_{10}$-alkoxy-$C_2-C_8$-alkyl, $C_1-C_8$-polyalkoxy-$C_2-C_8$-alkyl, $C_1-C_{10}$-alkylthio-$C_2-C_8$-alkyl, cycloalkyl having 3–8 ring atoms which can be interrupted by oxygen and/or sulphur, and phenyl or phenyl-$C_1-C_6$-alkyl, each of which is optionally substituted by halogen, $C_1-C_6$-alkyl, $C_1-C_6$-halogenoalkyl, $C_1-C_6$-alkoxy, $C_1-C_6$-halogenoalkoxy or nitro, or in which A and B together with the carbon atom to which they are bonded form a saturated or unsaturated, 3- to 8-membered ring which is optionally interrupted by oxygen and/or sulphur and optionally substituted by halogen, $C_1-C_6$-alkyl, $C_1-C_6$-alkoxy, $C_1-C_4$-halogenoalkyl, $C_1-C_4$-halogenoalkoxy, $C_1-C_4$-alkylthio or optionally substituted phenyl optionally benzo-fused, G represents hydrogen (a) or the groups

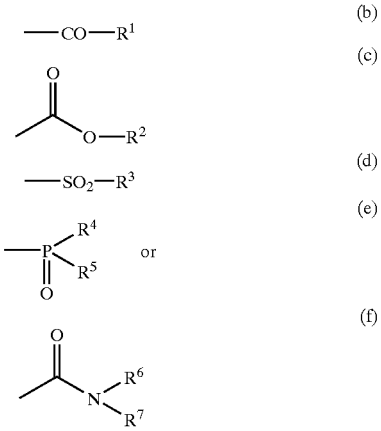

in which $R^1$ represents optionally halogen-substituted $C_1-C_{20}$-alkyl, $C_2-C_{20}$-alkenyl, $C_1-C_8$-alkoxy-$C_2-C_8$-alkyl, $C_1-C_8$-alkylthio-$C_2-C_8$-alkyl, $C_1-C_8$-polyalkoxy-$C_2-C_8$-alkyl or cycloalkyl having 3–8 ring atoms which can be interrupted by oxygen and/or sulphur atoms, phenyl which is optionally substituted by halogen, nitro, $C_1-C_6$-alkyl, $C_1-C_6$-alkoxy, $C_1-C_6$-halogenoalkyl or $C_1-C_6$-halogenoalkoxy;

phenyl-$C_1-C_6$-alkyl which is optionally substituted by halogen, $C_1-C_6$-alkyl, $C_1-C_6$-alkoxy, $C_1-C_6$-halogenoalkyl or $C_1-C_6$-halogenoalkoxy, pyridyl, pyrimidyl, thiazolyl and pyrazolyl, each of which is optionally substituted by halogen and/or $C_1-C_6$-alkyl, phenoxy-$C_1-C_6$-alkyl which is optionally substituted by halogen and/or $C_1-C_6$-alkyl, $R^2$ represents optionally halogen-substituted $C_1-C_{20}$-alkyl, $C_2-C_{20}$-alkenyl, $C_1-C_8$-alkoxy-$C_2-C_8$-alkyl or $C_1-C_8$-polyalkoxy-$C_2-C_8$-alkyl, phenyl or benzyl, each of which is optionally substituted by halogen, nitro, $C_1-C_6$-alkyl, $C_1-C_6$-alkoxy or $C_1-C_6$-halogenoalkyl, $R^3$, $R^4$ and $R^5$ independently of one another represent optionally halogen-substituted $C_1-C_8$-alkyl, $C_1-C_8$-alkoxy, $C_1-C_8$-alkylamino, di-($C_1-C_8$)-alkylamino, $C_1-C_8$-alkylthio, $C_2-C_5$-alkenylthio, $C_2-C_5$-alkinylthio or $C_3-C_7$-cycloalkylthio, or represent phenyl, phenoxy or phenylthio, each of which is optionally substituted by halogen, nitro, cyano, $C_1-C_4$-alkoxy, $C_1-C_4$-halogenoalkoxy, $C_1-C_4$-alkylthio, $C_1-C_4$-halogenoalkylthio, $C_1-C_4$-alkyl or $C_1-C_4$-halogenoalkyl, $R^6$ and $R^7$ independently of one another represent optionally halogen-substituted $C_1-C_{20}$-alkyl, $C_1-C_{20}$-alkoxy, $C_2-C_8$-alkenyl or $C_1-C_{20}$-alkoxy-$C_1-C_{20}$-alkyl, or represent phenyl which is optionally substituted by halogen, $C_1-C_{20}$-halogenoalkyl, $C_1-C_{20}$-alkyl or $C_1-C_{20}$-alkoxy, or represent benzyl which is optionally substituted by halogen, $C_1-C_{20}$-alkyl, $C_1-C_{20}$-halogenoalkyl or $C_1-C_{20}$-alkoxy, or together represent a $C_2-C_6$-alkylene ring which is optionally interrupted by oxygen, and A) (thio)phosphates, preferably 1. azinphos-methyl

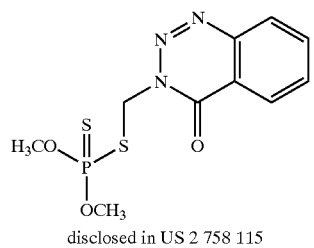

disclosed in US 2 758 115 and/or 2. chlorpyrifos

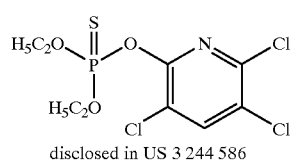

disclosed in US 3 244 586 and/or 3. diazinon

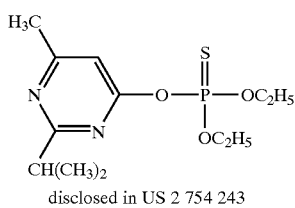

disclosed in US 2 754 243 and/or 4. dimethoate

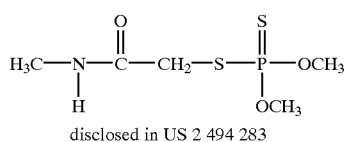

disclosed in US 2 494 283 and/or 5. disulfoton

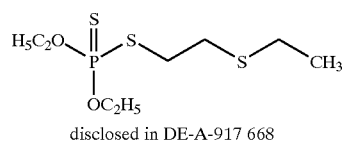

disclosed in DE-A-917 668 and/or 6. ethion

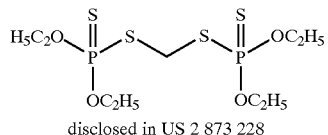

disclosed in US 2 873 228 and/or 7. fenitrothion

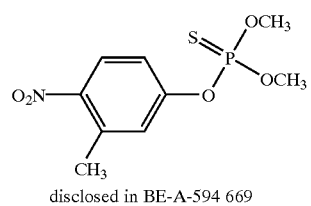

disclosed in BE-A-594 669 and/or 8. fenthion

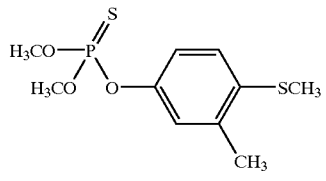

disclosed in DE-A-1 116 656 and/or 9. isoxathion

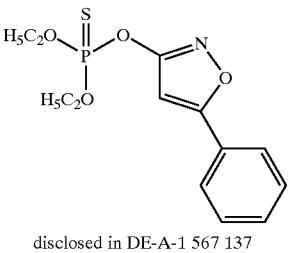

disclosed in DE-A-1 567 137 and/or 10. malathion

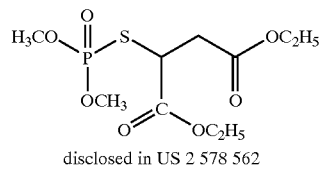

disclosed in US 2 578 562 and/or 11. methidathion

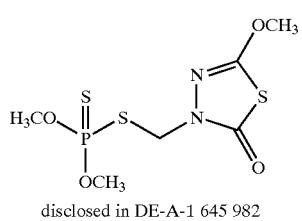

disclosed in DE-A-1 645 982 and/or 12. oxydemeton-methyl

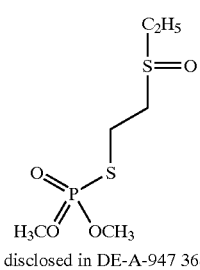

disclosed in DE-A-947 368 and/or 13. parathion

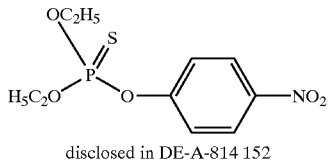

disclosed in DE-A-814 152 and/or 14. parathion-methyl

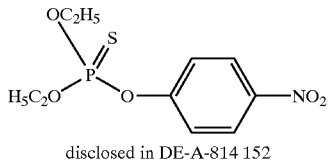

disclosed in DE-A-814 142 and/or 15. phenthoate

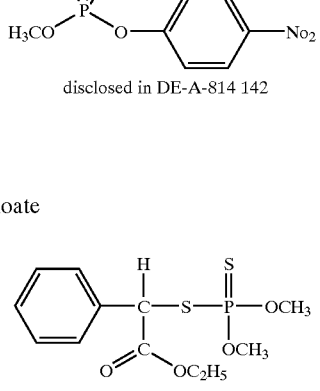

disclosed in GB-A-834 814 and/or 16. phorate

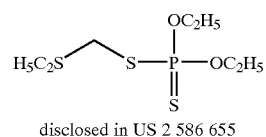

disclosed in US 2 586 655 and/or 17. phosalone

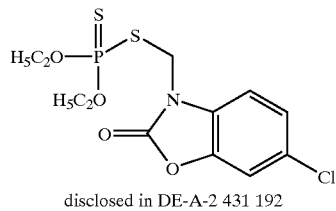

disclosed in DE-A-2 431 192 and/or 18. phosmet

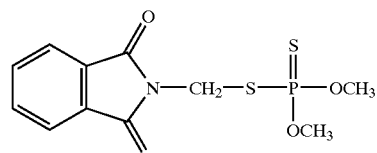

disclosed in US 2 767 194 and/or 19. phoxim

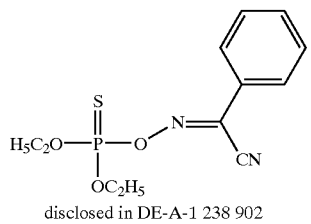

disclosed in DE-A-1 238 902 and/or 20. pirimiphos-methyl

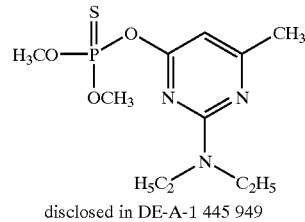

disclosed in DE-A-1 445 949 and/or 21. profenophos disclosed in DE-A-2 249 462 and/or
22. prothiophos disclosed in DE-A-2 111 414 and/or
23. tebupirimphos disclosed in DE-A-3 317 824 and/or
24. triazophos disclosed in DE-A-1 299 924 and/or
25. chlorfenvinphos disclosed in US-2 956 073 and/or 26. dichlorphos disclosed in GB-A-775 085 and/or
27. dicrotophos disclosed in BE-A-55 22 84 and/or
28. mevinphos disclosed in US-2 685 552 and/or
29. monocrotophos disclosed in DE-A-1 964 535 and/or
30. phosphamidon disclosed in US 2 908 605 and/or 31. acephate

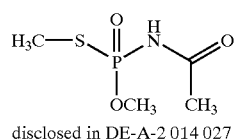

disclosed in DE-A-2 014 027 and/or
32. methamidophos

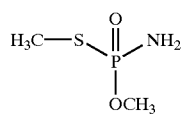

disclosed in US-3 309 266 and/or
33. trichlorfon

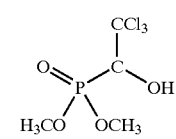

disclosed in US-2 701 225 and/or
B) pyrethroids, preferably
34. acrinathrin

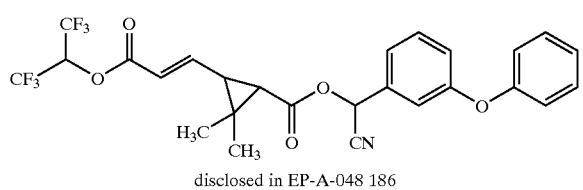

disclosed in EP-A-048 186 disclosed in EP-A-048 186
and/or
35. alpha-cypermethrin

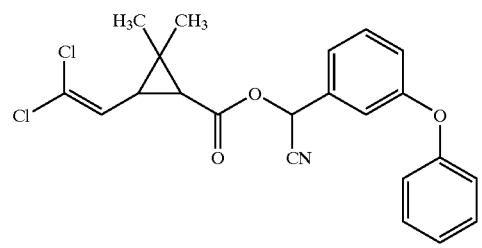

disclosed in EP-A-067 461 disclosed in EP-A-067 461
and/or 36. betacyfluthrin

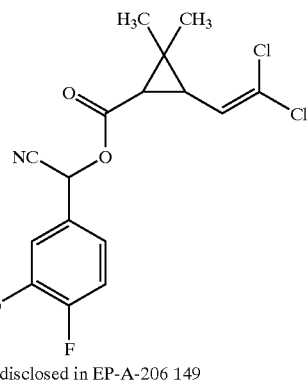

disclosed in EP-A-206 149 and/or
37. cyhalothrin

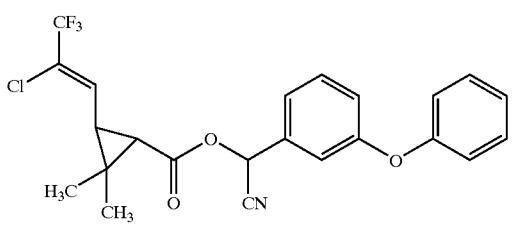

disclosed in DE-A-2 802 962 and/or
38. cypermethrin

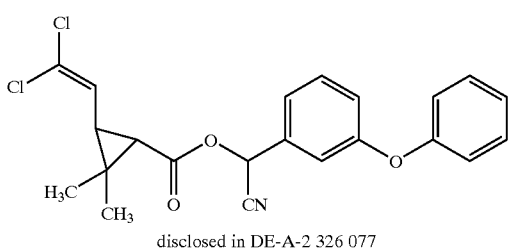

disclosed in DE-A-2 326 077 and/or
39. deltamethrin

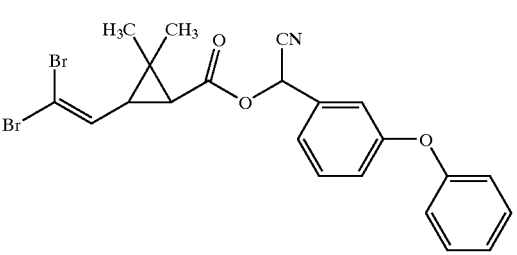

disclosed in DE-A-2 326 077 and/or 40. esfenvalerate
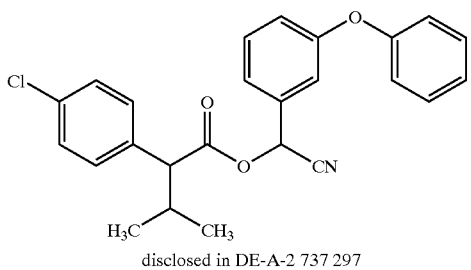
disclosed in DE-A-2 737 297
and/or
41. etofenprox
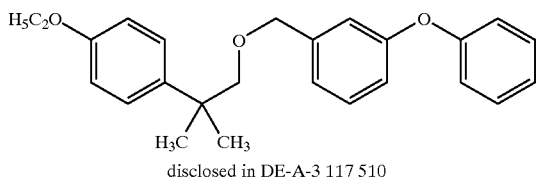
disclosed in DE-A-3 117 510
and/or
42. fenpropathrin
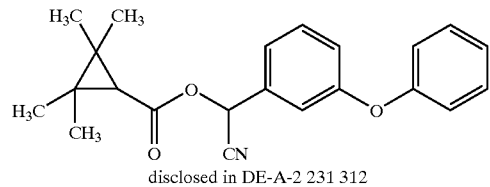
disclosed in DE-A-2 231 312
and/or
43. fenvalerate
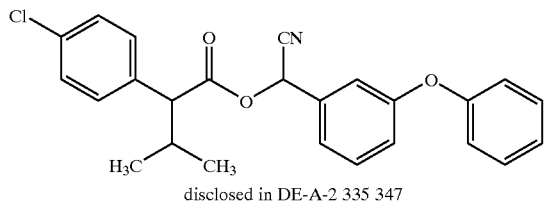
disclosed in DE-A-2 335 347
and/or
44. flucythrinate
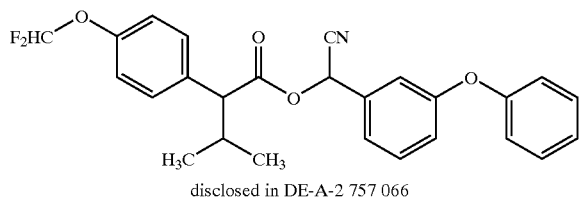
disclosed in DE-A-2 757 066
and/or
45. lambda-cyhalothrin
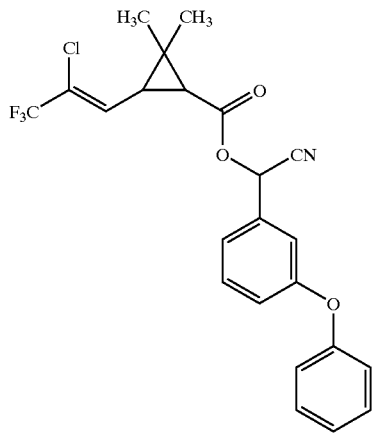
disclosed in EP-A-106 469
and/or
46. permethrin
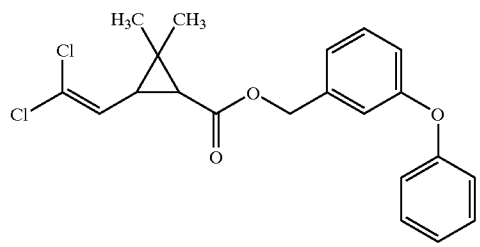
disclosed in DE-A-2 326 077
and/or
47. tau-fluvalinate
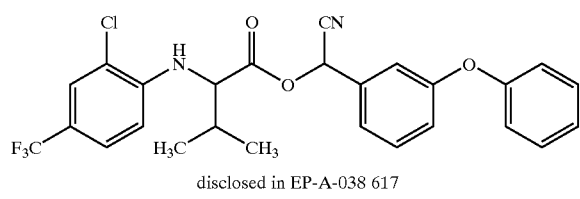
disclosed in EP-A-038 617
and/or
48. tralomethrin
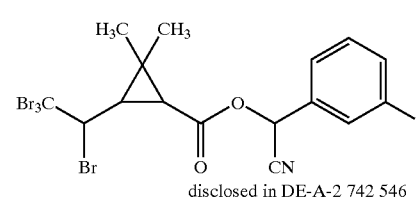
disclosed in DE-A-2 742 546
and/or 49. zeta-cypermethrin

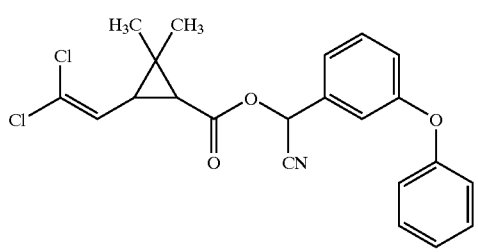

disclosed in EP-A-026 542 and/or
C) carbamates, preferably
50. carbaryl

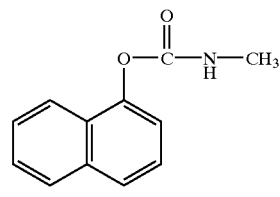

disclosed in US-2 903 478 and/or
51. fenoxycarb

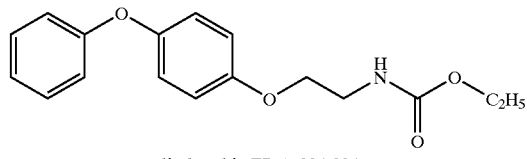

disclosed in EP-A-004 334 and/or
52. formetanate

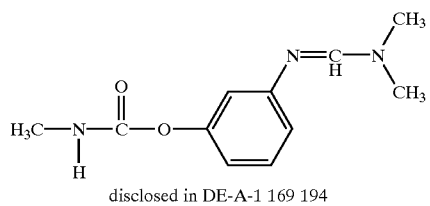

disclosed in DE-A-1 169 194 and/or
53. formetanate hydrochloride
disclosed in DE-A-1 169 194
and/or 54. methiocarb

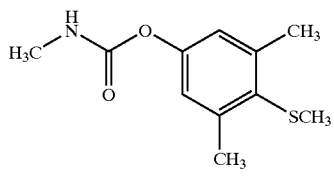

disclosed in DE-A-1 162 352 and/or
55. methomyl

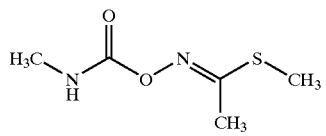

disclosed in US-3 639 620 and/or
56. oxamyl

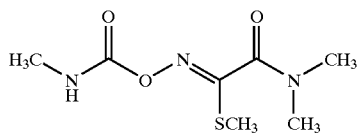

disclosed in DE-A-1 768 623 and/or
57. pirimicarb

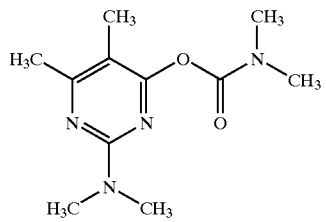

disclosed in GB-A-1 181 657 and/or
58. propoxur

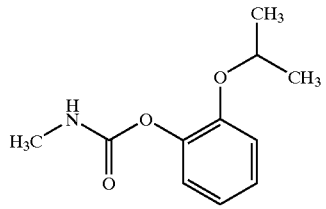

disclosed in DE-A-1 108 202 and/or 59. thiodicarb

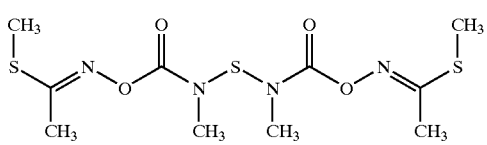

disclose in DE-A-2 530 439 and/or
D) benzoylureas, preferably
60. chlorfluazuron

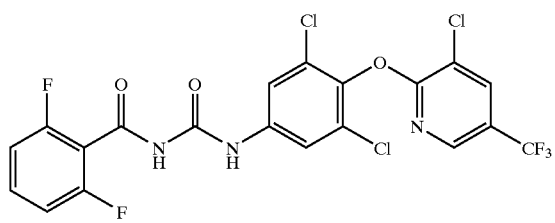

disclosed in DE-A-2 818 830 and/or
61. diflubenzuron

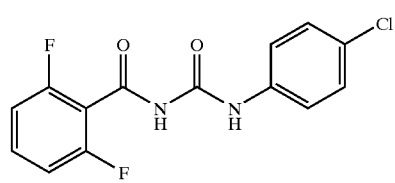

disclosed in DE-A-2 123 236 and/or
62. lufenuron

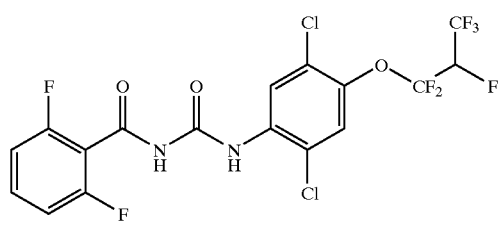

disclosed in EP-A-179 022 and/or
63. teflubenzuron

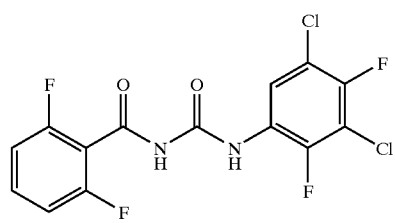

disclosed in EP-A-052 833 and/or 64. triflumuron

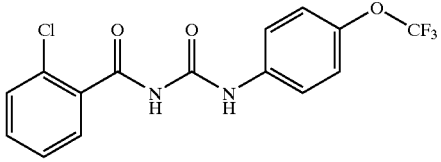

disclosed in DE-A-2 601 780 and/or
E) macrolides, preferably
65. ivermectin
and/or
66. emamectin
disclosed in EP-A-089 202
and/or
67. milbemectin
known from The Pesticide Manual, 11th Edition, 1997, p. 846
and/or
F) diacylhydrazines, preferably
68. methoxyfenozide

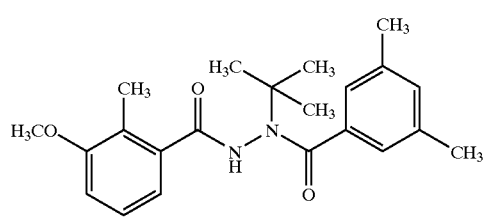

disclosed in EP-A-639 559 and/or
69. tebufenozide

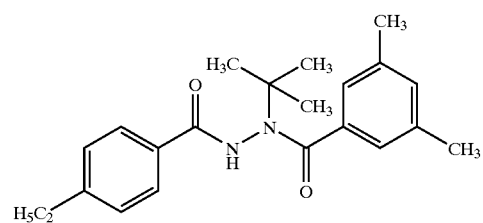

disclosed in EP-A-339 854 and/or
G) halogenocycloalkanes, preferably
70. endosulfan

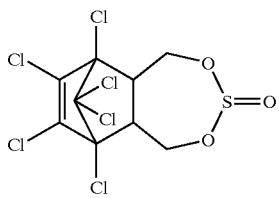

disclosed in DE-A-1 015 797 and/or 71 gamma-HCH

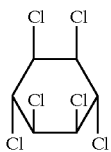

disclosed in US 2,502,258 and/or

H) acaricides, preferably 72. fenazaquin

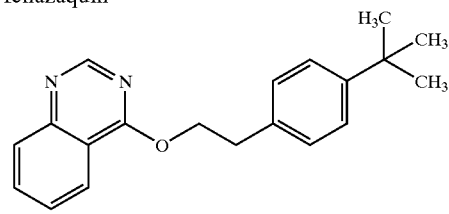

disclosed in EP-A-326 329 and/or 73. tebufenpyrad

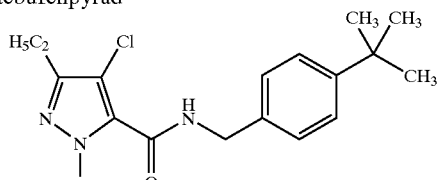

disclosed in EP-A-282 879 and/or 74. pyrimidifen

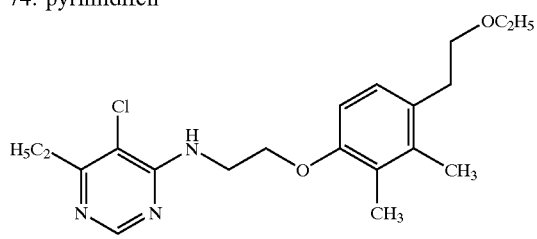

disclosed in EP-A-196 524 and/or 75. triarathene

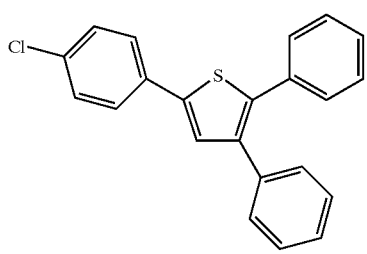

disclosed in DE-A-2 724 494 and/or 76. tetradifon

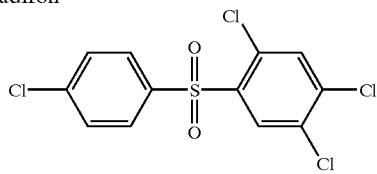

disclosed in US 2 812 281 and/or 77. propargite

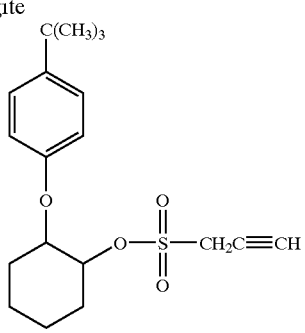

disclosed in US.3 272 854 and/or 78. hexythiazox

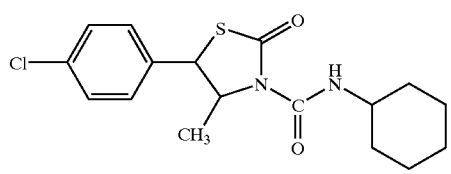

disclosed in DE-A-3 037 105 and/or 79. bromopropylate

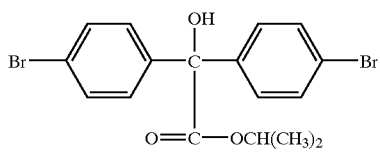

disclosed i US 3 784 696 and/or 80. 2-(acetyloxy)-3-dodecyl-1,4-naphthalenedione

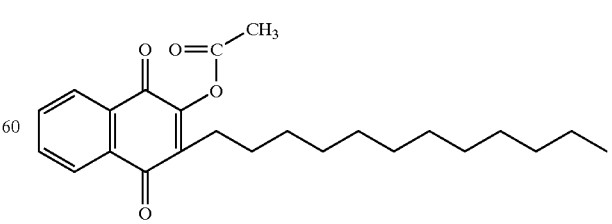

disclosed in DE-A-2 641 343 and/or 81. dicofol

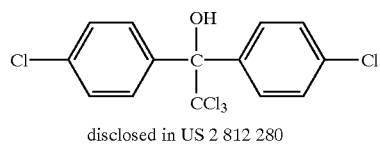

disclosed in US 2 812 280 and/or
I) other compounds such as
82. amitraz

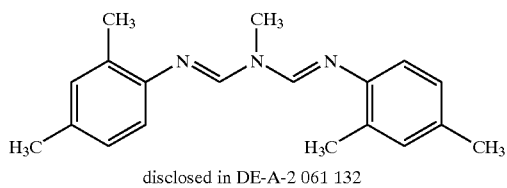

disclosed in DE-A-2 061 132 and/or
83. azadirachtin
  known from The Pesticide Manual, 11th Edition, 1997, p. 59
84. buprofezin

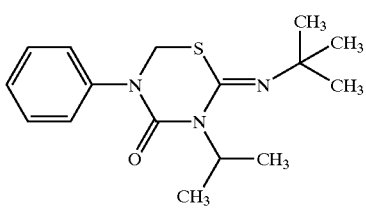

disclosed in DE-A-2 824 126 and/or
85. quinomethionate

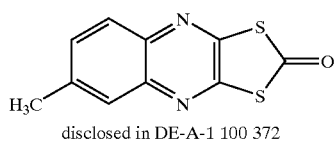

disclosed in DE-A-1 100 372 and/or
86. thiocyclam hydrogen oxalate

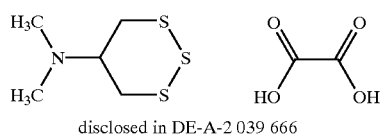

disclosed in DE-A-2 039 666 and/or 87. triazamate

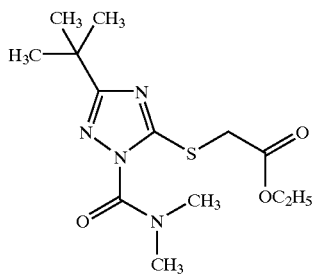

disclosed in EP-A-213 718 and/or
88. Trichogramma spp.
  known from The Pesticide Manual, 11th Edition, 1997, p. 1236
89. Verticiliium lecanii
  known from The Pesticide Manual, 11th Edition, 1997, p. 1266
90. fipronil

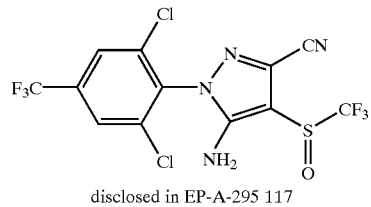

disclosed in EP-A-295 117 and/or
91. cyromazine

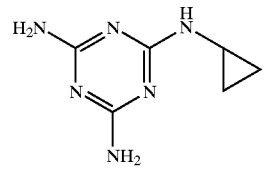

disclosed in DE-A-2 736 876 and/or
92. pymetrozin

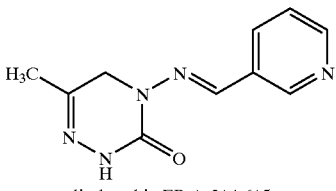

disclosed in EP-A-314 615

93. diofenolan

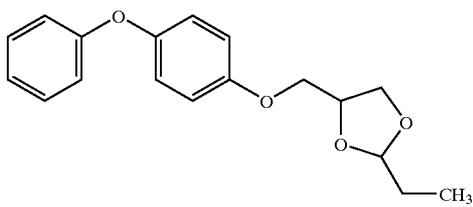

disclosed in DE-A 2 655 910 and/or
94. indoxacarb

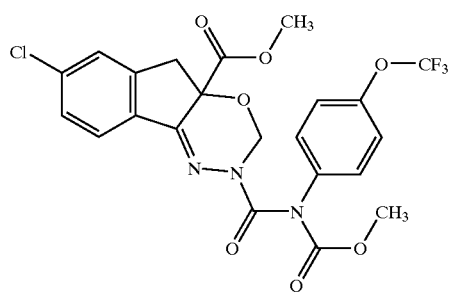

and/or
95. pyriproxyfen

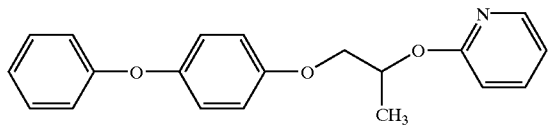

have very good insecticidal and acaricidal properties.

Preferred active compound combinations are those comprising compounds of the formula (I)
in which
X represents $C_1$–$C_4$-alkyl, halogen, $C_1$–$C_4$-alkoxy or $C_1$–$C_2$-halogenoalkyl,
Y represents hydrogen, $C_1$–$C_4$-alkyl, halogen, $C_1$–$C_4$-alkoxy or $C_1$–$C_2$-halogenoalkyl,
Z represents $C_1$–$C_4$-alkyl, halogen or $C_1$–$C_4$-alkoxy,
n represents 0 or 1,
A and B together with the carbon atom to which they are bonded form a saturated
5- to 6-membered ring which is optionally substituted by $C_1$–$C_4$-alkyl or $C_1$–$C_4$-alkoxy,
G represents hydrogen (a) or the groups

 (b)

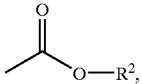 (c)

in which
$R^1$ represents optionally halogen-substituted $C_1$–$C_{16}$-alkyl, $C_2$–$C_{16}$-alkenyl, $C_1$–$C_6$-alkoxy-$C_2$–$C_6$-alkyl or cycloalkyl having 3–7 ring atoms which can be interrupted by 1 or 2 oxygen and/or sulphur atoms,
phenyl which is optionally substituted by halogen, nitro, $C_1$–$C_4$-alkyl, $C_1$–$C_4$-alkoxy, $C_1$–$C_3$-halogenoalkyl or $C_1$–$C_3$-halogenoalkoxy,
$R^2$ represents optionally halogen-substituted $C_1$–$C_{16}$-alkyl, $C_2$–$C_{16}$-alkenyl or $C_1$–$C_6$-alkoxy-$C_2$–$C_6$-alkyl, phenyl or benzyl, each of which is optionally substituted by halogen, nitro, $C_1$–$C_4$-alkyl, $C_1$–$C_4$-alkoxy or $C_1$–$C_4$-halogenoalkyl,
and at least one active compound of compounds 1 to 95.

Surprisingly, the insecticidal and acaricidal action of the active compound combination according to the invention considerably exceeds the total of the actions of the individual active compounds. A true synergistic effect which could not have been predicted exists, not just a complementation of action.

The active compound combinations according to the invention comprise at least one active compound of compounds 1 to 95, in addition to at least one active compound of the formula (I).

Especially preferred active compound combinations are those comprising the dihydrofuranone derivative of the formula (I-b-1)

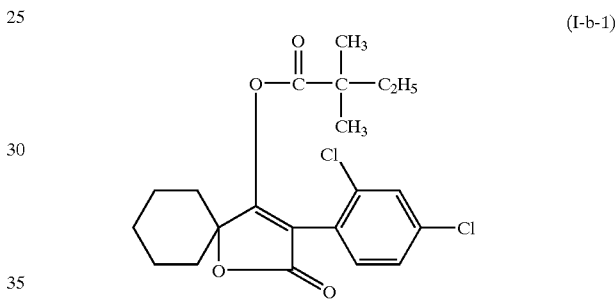

(I-b-1)

and at least one active compound of compounds 1 to 95.

In addition, the active compound combinations may also comprise other fungicidally, acaricidally or insecticidally active components which may be admixed.

If the active compounds are present in the active compound combinations according to the invention in certain weight ratios, the synergistic effect is particularly pronounced. However, the weight ratios of the active compounds in the active compound combinations may be varied within a relatively large range. In general, the combinations according to the invention comprise active compounds of the formula (I) and the other component in the mixing ratios indicated in the table hereinbelow as being preferred and especially preferred.

the mixing ratios are based on weight ratios. The ratio is to be understood as meaning active compound of the formula (I):other component

| Other component | Preferred mixing ratio | Especially preferred mixing ratio |
| --- | --- | --- |
| 2-(Acetyloxy)-3-dodecyl-1,4-naphthalini-done | 10:1 to 1:10 | 5:1 to 1:5 |
| Acephate | 10:1 to 1:10 | 5:1 to 1:5 |
| Acrinathrin | 20:1 to 1:50 | 10:1 to 1:1 |
| Alpha-cypermethrin | 50:1 to 1:5 | 10:1 to 1:1 |
| Amitraz | 5:1 to 1:20 | 1:1 to 1:10 |
| Azadirachtin | 50:1 to 1:5 | 10:1 to 1:1 |

-continued

| Other component | Preferred mixing ratio | Especially preferred mixing ratio |
|---|---|---|
| Azinphos-methyl | 10:1 to 1:10 | 5:1 to 1:5 |
| Betacyfluthrin | 50:1 to 1:5 | 10:1 to 1:1 |
| Bromopropylate | 10:1 to 1:10 | 5:1 to 1:5 |
| Buprofezin | 10:1 to 1:10 | 5:1 to 1:5 |
| Carbaryl | 10:1 to 1:10 | 5:1 to 1:5 |
| Quinomethionate | 10:1 to 1:10 | 5:1 to 1:5 |
| Chlorfenvinphos | 10:1 to 1:10 | 5:1 to 1:5 |
| Chlorfluazuron | 10:1 to 1:10 | 5:1 to 1:5 |
| Chlorpyrifos | 10:1 to 1:10 | 5:1 to 1:5 |
| Cyhalothrin | 50:1 to 1:5 | 10:1 to 1:1 |
| Cypermethrin | 50:1 to 1:5 | 10:1 to 1:1 |
| Cyromazine | 10:1 to 1:10 | 5:1 to 1:5 |
| Deltamethrin | 50:1 to 1:5 | 10:1 to 1:1 |
| Diazinon | 10:1 to 1:10 | 5:1 to 1:5 |
| Dichlorphos | 10:1 to 1:10 | 5:1 to 1:5 |
| Dicofol | 10:1 to 1:10 | 5:1 to 1:5 |
| Dicrotophos | 10:1 to 1:10 | 5:1 to 1:5 |
| Diflubenzuron | 10:1 to 1:10 | 5:1 to 1:5 |
| Dimethoate | 10:1 to 1:10 | 5:1 to 1:5 |
| Diofenolan | 100:1 to 1:2 | 20:1 to 1:1 |
| Disulfoton | 10:1 to 1:10 | 5:1 to 1:5 |
| Emamectin | 50:1 to 1:5 | 10:1 to 1:1 |
| Endosulfan | 10:1 to 1:10 | 5:1 to 1:5 |
| Esfenvalerate | 50:1 to 1:5 | 10:1 to 1:1 |
| Ethion | 10:1 to 1:10 | 5:1 to 1:5 |
| Etofenprox | 10:1 to 1:10 | 5:1 to 1:5 |
| Fenazaquin | 10:1 to 1:10 | 5:1 to 1:5 |
| Fenitrothion | 10:1 to 1:10 | 5:1 to 1:5 |
| Fenoxycarb | 10:1 to 1:10 | 5:1 to 1:5 |
| Fenpropathrin | 10:1 to 1:10 | 5:1 to 1:5 |
| Fenpyrad (tebufenpyrad) | 10:1 to 1:10 | 5:1 to 1:5 |
| Fenthion | 20:1 to 1:10 | 5:1 to 1:5 |
| Fenvalerate | 20:1 to 1:5 | 10:1 to 1:1 |
| Fipronil | 10:1 to 1:10 | 5:1 to 1:5 |
| Flucythrinate | 50:1 to 1:5 | 10:1 to 1:1 |
| Formetanate | 10:1 to 1:10 | 5:1 to 1:5 |
| Hexythiazox | 20:1 to 1:5 | 10:1 to 1:2 |
| Indoxacarb | 50:1 to 1:5 | 20:1 to 1:2 |
| Isoxathion | 10:1 to 1:10 | 5:1 to 1:5 |
| Ivermectin | 50:1 to 1:5 | 10:1 to 1:1 |
| Lambda-cyhalothrin | 50:1 to 1:5 | 10:1 to 1:1 |
| Lindane (gamma-HCH) | 10:1 to 1:10 | 5:1 to 1:5 |
| Lufenuron | 20:1 to 1:5 | 10:1 to 1:2 |
| Malathion | 10:1 to 1:10 | 5:1 to 1:5 |
| Methamidophos | 10:1 to 1:10 | 5:1 to 1:5 |
| Methidathion | 10:1 to 1:10 | 5:1 to 1:5 |
| Methiocarb | 10:1 to 1:10 | 5:1 to 1:5 |
| Methomyl | 10:1 to 1:10 | 5:1 to 1:5 |
| Methoxyfenozide | 10:1 to 1:10 | 5:1 to 1:5 |
| Mevinphos | 10:1 to 1:10 | 5:1 to 1:5 |
| Milbemectin | 50:1 to 1:5 | 10:1 to 1:1 |
| Monocrotophos | 10:1 to 1:10 | 5:1 to 1:5 |
| Oxamyl | 5:1 to 1:100 | 1:1 to 1:20 |
| Oxydemeton-methyl | 10:1 to 1:10 | 5:1 to 1:5 |
| Parathion | 10:1 to 1:10 | 5:1 to 1:5 |
| Parathion-methyl | 10:1 to 1:10 | 5:1 to 1:5 |
| Permethrin | 10:1 to 1:10 | 5:1 to 1:5 |
| Phenthoate | 10:1 to 1:10 | 5:1 to 1:5 |
| Phorate | 10:1 to 1:10 | 5:1 to 1:5 |
| Phosalone | 10:1 to 1:10 | 5:1 to 1:5 |
| Phosmet | 10:1 to 1:10 | 5:1 to 1:5 |
| Phosphamidon | 10:1 to 1:10 | 5:1 to 1:5 |
| Phoxim | 10:1 to 1:10 | 5:1 to 1:5 |
| Pirimicarb | 10:1 to 1:10 | 5:1 to 1:5 |
| Pirimiphos-methyl | 10:1 to 1:10 | 5:1 to 1:5 |
| Profenophos | 10:1 to 1:10 | 5:1 to 1:5 |
| Propargite | 10:1 to 1:10 | 5:1 to 1:5 |
| Propoxur | 10:1 to 1:10 | 5:1 to 1:5 |
| Prothiophos | 10:1 to 1:10 | 5:1 to 1:5 |
| Pymetrozin | 10:1 to 1:10 | 5:1 to 1:5 |
| Pyrimidifen | 50:1 to 1:5 | 10:1 to 1:1 |
| Pyriproxyfen | 10:1 to 1:10 | 5:1 to 1:5 |
| Tau-fluvalinate | 20:1 to 1:5 | 10:1 to 1:2 |
| Tebufenozide | 10:1 to 1:10 | 5:1 to 1:5 |
| Tebupirimphos | 10:1 to 1:10 | 5:1 to 1:5 |

-continued

| Other component | Preferred mixing ratio | Especially preferred mixing ratio |
|---|---|---|
| Teflubenzuron | 20:1 to 1:5 | 10:1 to 1:2 |
| Tetradifon | 10:1 to 1:10 | 5:1 to 1:5 |
| Thiocyclam | 5:1 to 1:20 | 1:1 to 1:10 |
| Thiodicarb | 5:1 to 1:20 | 1:1 to 1:10 |
| Tralomethrin | 50:1 to 1:5 | 10:1 to 1:1 |
| Triarathene | 5:1 to 1:20 | 1:1 to 1:10 |
| Triazamate | 10:1 to 1:10 | 5:1 to 1:5 |
| Triazophos | 5:1 to 1:20 | 1:1 to 1:10 |
| Trichlorfon | 10:1 to 1:10 | 5:1 to 1:5 |
| Trichogramma spp. | | |
| Triflumuron | 10:1 to 1:10 | 5:1 to 1:5 |
| Verticillium lecanii | | |
| Zeta-cypermethrin | 50:1 to 1:5 | 10:1 to 1:2 |

The active compound combinations according to the invention are suitable for controlling animal pests, preferably arthropods and nematodes, in particular insects and arachnids found in agriculture, in afforestations, in the protection of stored product and materials and in the hygiene sector. They are active against normally sensitive and resistant species, and against all or individual developmental stages. The abovementioned pests include:

From the order of the Isopoda, for example, *Oniscus asellus*, Armadillidium vulgare, Porcellio scaber.

From the order of the Diplopoda, for example, *Blaniulus guttulatus*.

From the order of the Chilopoda, for example, *Geophilus carpophagus, Scutigera spp.*

From the order of the Symphyla, for example, *Scutigerella immaculata*.

From the order of the Thysanura, for example, *Lepisma saccharina*.

From the order of the Collembola, for example, *Onychiurus armatus*.

From the order of the Orthoptera, for example, *Acheta domesticus,* Gryllotalpa spp., *Locusta migratoria migratorioides,* Melanoplus spp., *Schistocerca gregaria.*

From the order of the Blattaria, for example, *Blatta orientalis, Periplaneta americana, Leucophaea maderae, Blattella germanica.*

From the order of the Dermaptera, for example, *Forficula auricularia.*

From the order of the Isoptera, for example, Reticulitermes spp..

From the order of the Phthiraptera, for example, *Pediculus humanus corporis,* Haematopinus spp., Linognathus spp., Trichodectes spp., Damalinia spp..

From the order of the Thysanoptera, for example, *Hercinothrips femoralis, Thrips tabaci, Thrips palmi, Frankliniella accidentalis.*

From the order of the Heteroptera, for example, Euryga-ster spp., *Dysdercus intermedius, Piesma quadrata, Cimex lectularius, Rhodnius prolixus,* Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastratix,* Pemphigus spp., *Macrosiphum avenae,* Myzus spp., *Phorodon humuli, Rhopalosiphum padi,* Empoasca spp., *Euscelis* bilobatus, Nephotettix cincticeps, Lecanium corni, Saissetia oleae, Laodelphax striatellus, Nilaparvata lugens, Aonidiella aurantii, Aspidiotus hederae, Pseudococcus spp., Psylla spp..

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Mamestra brassicae, Panolis flammea,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana,* Cnaphalocerus spp., *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis, Costelytra zealandica, Lissorhoptrus oryzophilus.*

From the order of the Hymenoptera, for example, Diprion spp., Hoplocampa spp., Lasius spp., *Monomorium pharaonis,* Vespa spp..

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae, Tipula paludosa,* Hylemyia spp., Liriomyza spp..

From the order of the Siphonaptera, for example, *Xenopsylla cheopis,* Ceratophyllus spp..

From the class of the Arachnida, for example, *Scorpio maurus, Latrodectus mactans, Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp., Tetranychus spp., Hemitarsonemus spp., Brevipalpus spp..

The plant-parasitic nematodes include, for example, Pratylenchus spp., *Radopholus similis, Ditylenchus dipsaci, Tylenchulus semipenetrans,* Heterodera spp., Globodera spp., Meloidogyne spp., Aphelenchoides spp., Longidorus spp., Xiphinema spp., Trichodorus spp., Bursaphelenchus spp..

The active compound combinations can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants, and/or foam formers.

In the case of the use of water as an extender, organic solvents can, for example, also be used as cosolvents. The following are essentially suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Suitable solid carriers are:
for example ammonium salts and ground natural minerals such as kaolins, clays, talc, chalk, quartz, attapulgite, montmorillonite or diatomaceous earth, and ground synthetic materials such as highly-disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic colorants such alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

The active compound combinations according to the invention can be present in their commercially available formulations and in the use forms, prepared from these formulations, as a mixture with other active compounds, such as insecticides, attractants, sterilants, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms.

Mixtures with other known active compounds such as herbicides or with fertilizers and growth regulators are also possible.

When used as insecticides, the active compound combinations according to the invention can furthermore be present in their commercially available formulations and in the use forms, prepared from these formulations, as a mixture with synergists. Synergists are compounds which increase the action of the active compounds, without it being necessary for the synergist added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and stored-product pests, the active compound combinations are distinguished by an excellent residual action on wood and clay as well as a good stability to alkali on limed substrates.

The active compound combinations according to the invention are not only active against plant pests, hygiene pests and stored-product pests, but also, in the veterinary medicine sector, against animal parasites (ectoparasites) such as hard ticks, soft ticks, mange mites, harvest mites, flies (stinging and licking), parasitizing fly larvae, lice, hair lice, bird lice and fleas. These parasites include:

From the order of the Anoplurida, for example, Haematopinus spp., Linognathus spp., Pediculus spp., Phtirus spp., Solenopotes spp..

From the order of the Mallophagida and the suborders Amblycerina and Ischnocerina, for example, Trimenopon spp., Menopon spp., Trinoton spp., Bovicola spp., Werneckiella spp., Lepikentron spp., Damalina spp., Trichodectes spp., Felicola spp..

From the order Diptera and the suborders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp., Melophagus spp.

From the order of the Siphonapterida, for example, Pulex spp., Ctenocephalides spp., Xenopsylla spp., Ceratophyllus spp..

From the order of the Heteropterida, for example, Cimex spp., Triatoma spp., Rhodnius spp., Panstrongylus spp.

From the order of the Blattarida, for example, *Blatta orientalis, Periplaneta americana, Blattella germanica,* Supella spp..

From the subclass of the Acaria (Acarida) and the order of the Meta- and Mesostigmata, for example, Argas spp., Ornithodorus spp., Otobius spp., Ixodes spp., Amblyomma spp., Boophilus spp., Dermacentor spp., Haemophysalis spp., Hyalomma spp., Rhipicephalus spp., Dermanyssus spp., Raillietia spp., Pneumonyssus spp., Sternostoma spp., Varroa spp..

From the order of the Actinedida (Prostigmata) and Acaridida (Astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp., Laminosioptes spp..

The active compound combinations according to the invention are also suitable for controlling arthropods which attack agricultural livestock such as, for example, cattle, sheep, goats, horses, pigs, donkeys, camels, buffaloes, rabbits, chickens, turkeys, ducks, geese, honey bees, other domestic animals such as, for example, dogs, cats, caged birds, aquarium fish and so-called experimental animals such as, for example, hamsters, guinea pigs, rats and mice. By controlling these arthropods, cases of death and reductions in productivity (for meat, milk, wool, hides, eggs, honey and the like) should be diminished, so that more economical and simpler animal husbandry is possible by the use of the active compound combinations according to the invention.

The active compound combinations according to the invention are used in the veterinary sector in a known manner by enteral administration in the form of, for example, tablets, capsules, potions, drenches, granules, pastes, boluses, the feed-through method, suppositories, by parenteral administration such as, for example, by injections (intramuscularly, subcutaneously, intravenously, intraperitoneally and the like), implants, by nasal administration, by dermal administration in the form of, for example, immersing or dipping, spraying, pouring-on, spotting-on, washing, dusting, and with the aid of active-compound-comprising moulded articles such as collars, ear tags, tail tags, limb bands, halters, marking devices and the like.

When used for cattle, poultry, domestic animals and the like, the active compound combinations can be applied as formulations (for example powders, emulsions, flowables) comprising the active compounds in an amount of 1 to 80% by weight, either directly or after 100- to 10,000-fold dilution, or they may be used as a chemical dip.

Moreover, it has been found that the active compound combinations according to the invention show a potent insecticidal action against insects which destroy industrial materials.

The following insects may be mentioned by way of example and with preference, but not by way of limitation:

Beetles such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis,* Xyleborus spec., Tryptodendron spec., *Apate monachus, Bostrychus capucins, Heterobostrychus brunneus,* Sinoxylon spec., *Dinoderus minutus.*

Dermapterans such as

*Sirex juvencus, Urocerus gigas, Urocerus gigas taignus, Urocerus augur.*

Termites such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristle tails such as Lepisma saccharina.

Industrial materials in the present context are understood as meaning non-living materials such as, preferably, polymers, adhesives, glues, paper and board, leather, wood, timber products and paints.

The material which is to be protected from insect attack is very especially preferably wood and timber products.

Wood and timber products which can be protected by the composition according to the invention, or mixtures comprising it, are to be understood as meaning, for example:

Construction timber, wooden beams, railway sleepers, bridge components, jetties, vehicles made of wood, boxes, pallets, containers, telephone poles, wood lagging, windows and doors made of wood, plywood, clipboard, joinery, or timber products which quite generally are used in house construction or building joinery.

The active compound combinations can be used as such, in the form of concentrates or generally customary formulations such as powders, granules, solutions, suspensions, emulsions or pastes.

The abovementioned formulations can be prepared in a manner known per se, for example by mixing the active compounds with at least one solvent or diluent, emulsifier, dispersant and/or binder or fixative, water repellant, if desired desiccants and UV stabilizers, and if desired colorants and pigments and other processing auxiliaries.

The insecticidal compositions or concentrates used for protecting wood and timber products comprise the active compound according to the invention in a concentration of 0.0001 to 95% by weight, in particular 0.001 to 60% by weight.

The amount of composition or concentrate employed depends on the species and the abundance of the insects and on the medium. The optimal quantity to be employed can be determined in each case by test series upon application. In general, however, it will suffice to employ 0.0001 to 20% by weight, preferably 0.001 to 10% by weight, of the active compound, based on the material to be protected.

A suitable solvent and/or diluent is an organochemical solvent or solvent mixture and/or an oily or oil-type organochemical solvent or solvent mixture of low volatility and/or a polar organochemical solvent or solvent mixture and/or water and, if appropriate, an emulsifier and/or wetter.

Organochemical solvents which are preferably employed are oily or oil-type solvents with an evaporation number of above 35 and a flash point of above 30° C., preferably above 45° C. Such oily and oil-type solvents which are insoluble in water and of low volatility and which are used are suitable mineral oils or their aromatic fractions or mineral-oil-containing solvent mixtures, preferably white spirit, petroleum and/or alkylbenzene.

Mineral oils which are advantageously used are those with a boiling range of 170 to 220° C., white spirit with a boiling range of 170 to 220° C., spindle oil with a boiling range of 250 to 350° C., petroleum and aromatics with a boiling range of 160 to 280° C., oil of terpentine, and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene are used.

The organic oily or oil-type solvents of low volatility and with an evaporation number-of above 35 and a flash point of above 30° C., preferably above 45° C., can be replaced in part by organochemical solvents of high or medium volatility, with the proviso that the solvent mixture also has an evaporation number of above 35 and a flash point of above 30° C., preferably above 45° C., and that the insecticide/fungicide mixture is soluble or emulsifiable in this solvent mixture.

In a preferred embodiment, some of the organochemical solvent or solvent mixture is replaced by an aliphatic polar organochemical solvent or solvent mixture. Aliphatic organochemical solvents which contain hydroxyl and/or ester and/or ether groups are preferably used, such as, for example, glycol ethers, esters or the like.

Organochemical binders used for the purposes of the present invention are the synthetic resins and/or binding drying oils which are known per se and which can be diluted in water and/or dissolved or dispersed or emulsified in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin such as indene/coumarone resin, silicone resin, drying vegetable and/or drying oils and/or physically drying binders based on a natural and/or synthetic resin.

The synthetic resin employed as binder can be employed in the form of an emulsion, dispersion or solution. Bitumen or bituminous substances may also be used as binders, in amounts of up to 10% by weight. In addition, colorants, pigments, water repellants, odour-masking agents, and inhibitors or anticorrosive agents and the like, all of which are known per se, can be employed.

In accordance with the invention, the composition or the concentrate preferably comprises, as organochemical binders, at least one alkyl resin or modified alkyl resin and/or a drying vegetable oil. Alkyd resins which are preferably used in accordance with the invention are those with an oil content of over 45% by weight, preferably 50 to 68% by weight.

Some or all of the abovementioned binder can be replaced by a fixative (mixture) or plasticizer (mixture). These additives are intended to prevent volatilization of the active compounds, and also crystallization or precipitation. They preferably replace 0.01 to 30% of the binder (based on 100% of binder employed).

The plasticizers are from the chemical classes of the phthalic esters, such as dibutyl phthalate, dioctyl phthalate or benzyl butyl phthalate, phosphoric esters such as tributyl phosphate, adipic esters such as di-(2-ethylhexyl)-adipate, stearates such as butyl stearate or amyl stearate, oleates such as butyl oleate, glycerol ethers or higher-molecular-weight glycol ethers, glycerol esters and p-toluenesulphonic esters.

Fixatives are based chemically on polyvinyl alkyl ethers such as, for example, polyvinyl methyl ether, or ketones such as benzophenone and ethylenebenzophenone.

Other suitable solvents or diluents are, in particular, also water, if appropriate as a mixture with one or more of the abovementioned organochemical solvents or diluents, emulsifiers and dispersants.

Particularly effective timber protection is achieved by industrial-scale impregnating processes, for example the vacuum, double-vacuum or pressure processes.

The active compound combinations according to the invention can also be employed for protecting objects which come into contact with saltwater or brackish water, such as hulls, screens, nets, buildings, moorings and signalling systems, from fouling.

Fouling by sessile Oligochaeta, such as Serpulidae, and by shells and species from the Ledamorpha group (goose barnacles), such as various Lepas and Scalpellum species, or by species from the Balanomorpha group (acorn barnacles), such as Balanus or Pollicipes species, increases the frictional drag of ships and, as a consequence, leads to a marked increase in operation costs owing to higher energy consumption and additionally frequent residence in the dry dock.

Apart from fouling by algae, for example Ectocarpus sp. and Ceramium sp., fouling by sessile Entomostraka groups, which come under the generic term Cirripedia (cirriped crustaceans), is of particular importance.

Surprisingly, it has now been found that the active compound combinations according to the invention have an outstanding antifouling action.

Using the active compound combinations according to the invention, the use of heavy metals such as, for example, in bis(trialkyltin) sulphides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulphide, antimony oxide, polymeric butyl titanate, phenyl-(bispyridine)-bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bis-dimethyldithiocarbamoylzinc ethylenebisthiocarbamate, zinc oxide, copper(I) ethylene-bisdithiocarbamate, copper thiocyanate, copper naphthenate and tributyltin halides can be dispensed with, or the concentration of these compounds substantially reduced.

If appropriate, the ready-to-use antifouling paints can additionally comprise other active compounds, preferably algicides, fungicides, herbicides, molluscicides, or other antifouling active compounds.

Preferably suitable components in combinations with the antifouling compositions according to the invention are:
algicides such as
  2-tert.-butylamino4-cyclopropylamino-6-methylthio-1,3,5-triazine, dichlorophen, diuron, endothal, fentine acetate, isoproturon, methabenzthiazuron, oxyfluorfen, quinoclamine and terbutryn;
fungicides such as
  benzo[b]thiophenecarboxylic acid cyclohexylamide S,S-dioxide, dichlofluanid, fluor-folpet, 3-iodo-2-propinyl butylcarbamate, tolylfluanid and azoles such as azaconazole, cyproconazole, epoxyconazole, hexaconazole, metconazole, propiconazole and tebuconazole;
molluscicides such as
  fentin acetate, metaldehyde, methiocarb, niclosamid, thiodicarb and trimethacrb;
or conventional antifouling active compounds such as
  4,5-dichloro-2-octyl-4-isothiazolin-3-one, diiodomethylparatryl sulfone, 2-(N,N-dimethylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulfonyl)-pyridine, 2,4,5,6-tetrachloroisophthalonitrile, tetrame-thylthiuram disulfide and 2,4,6-trichlorophenylmaleiimide.

The antifouling compositions used comprise the active compound combinations according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730–732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably soluble in salt water. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compound combinations are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus,* Bryobia ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, Aviculariidae, Araneidae.

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus,* Polydesmus From the order of the Chilopoda, for example, Geophilus spp..

From the order of the Zygentoma, for example, Ctenolepisma spp., *Lepisma saccharina, Lepismodes inquilinus.*

From the order of the Blattaria, for example, *Blatta orientalies, Blattella germanica, Blattella asahinai, Leucophaea maderae,* Panchlora spp., Parcoblatta spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, Kalotermes spp., Reticulitermes spp.

From the order of the Psocoptera, for example, Lepinatus spp., Liposcelis spp.

From the order of the Coleptera, for example, Anthrenus spp., Attagenus spp., Dermestes spp., *Latheticus oryzae,* Necrobia spp., Ptinus spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus,* Anopheles spp., *Calliphora erythrocephala, Chrysozona pluvialis, Culex quinquefasciatus, Culex pipiens, Culex tarsalis,* Drosophila spp., *Fannia canicularis, Musca domestica,* Phlebotomus spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis,* Paravespula spp., *Tetramorium caespitum.*

From the order of the Anoplura, for example, *Pediculus humanus capitis, Pediculus humanus corporis, Phthirus pubis.*

From the order of the Heteroptera, for example, *Cimex hemipterus, Cimex lectularius, Rhodinus prolixus, Triatoma infestans.*

They are used as aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

All plants and plant parts can be treated in accordance with the invention. Plants are to be understood as meaning in the present context all plants and plant populations such as desired and undesired wild plants or crop plants (inclusive of naturally occurring crop plants). Crop plants can be plants which can be obtained by conventional plant breeding and optimization methods or by biotechnological and recombinant methods or by combinations of these methods, inclusive of the transgenic plants and inclusive of the plant varieties protectable or not protectable by plant breeders' rights, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

Treatment according to the invention of the plants and plant parts with the active compounds is carried out directly or by allowing the compounds to act on the surroundings, environment or storage space by the customary treatment methods, for example by immersion, spraying, evaporation, fogging, scattering, painting on and, in the case of propagation material, in particular in the case of seed, also by applying one or more coats.

The good insecticidal and acaricidal action of the active compound combinations according to the invention can be seen from the examples which follow. While the individual active compounds show weaknesses in their action, the combinations show an action which exceeds a simple sum of actions.

A synergistic effect in insecticides and acaricides is always present when the action of the active compound combinations exceeds the total of the actions of the active compounds when applied individually.

The expected action for a given combination of two active compounds can be calculated as follows, using the formula of S. R. Colby, Weeds 15 (1967), 20–22:

If
X is the efficacy when employing active compound A at an application rate of m g/ha or in a concentration of m ppm, Y is the efficacy when employing active compound B at an application rate of n g/ha or in a concentration of n ppm and E is the efficacy when employing active compounds A and B at application rates of m and n g/ha or in a concentration of m and n ppm, then $$E = X + Y - \frac{X \cdot Y}{100}$$

The efficacy is determined in %. 0% means an efficacy which corresponds to that of the control, while an efficacy of 100% means that no infection/infestation is observed.

If the actual action exceeds the calculated value, the action of the combination is superadditive, i.e. a synergistic effect is present. In this case, the actually observed efficacy must exceed the value calculated using the above formula for the expected efficacy (E).

USE EXAMPLES

Example A

Heliothis Virescens Test solvent: 7 parts by weight of dimethylformamide emulsifier: 1 part by weight of alkylaryl polyglycol ether To produce a suitable active compound preparation, 1 part by weight of active compound is mixed with the stated amounts of solvent and emulsifier, and the concentrate is diluted with emulsifier-containing water to the desired concentration. Soya bean shoots (*Glycine max*) are treated by immersion in the active compound preparation of the desired concentration and are populated with *Heliothis virescens* caterpillars while the leaves are still moist.

After the desired period, the destruction is determined in %. 100% means that all caterpillars have been killed; 0% means that none of the caterpillars have been killed. The kill figures determined are calculated using Colby's formula.

In this test, a synergistically increased efficacy in comparison with the active compounds when applied individually is shown, for example, by the following active compound combination in accordance with the present application:

TABLE A

| | plant-injurious insects Heliothis virescens test | |
|---|---|---|
| Active compounds | Active compound concentration In ppm | Percentage destruction after 3 days |
| Ex. (I-b-1) known | 0.32 | 0 |
| Betacyfluthrin known | 0.32 | 75 |
| Ex. (I-b-1) + betacyfluthrin (1:1) according to the invention | 0.32 + 0.32 | found* calc.** 100    75 |

*found = found action
**calc. = action calculated using Colby's formula

Example B

Nephotettix Test solvent: 7 parts by weight of dimethylformamide
emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Rice seedlings (*Oryza sativa*) are treated by immersion in the active compound preparation of the desired concentration and are populated with green rice leaf-hoppers (Nephotettix cincticeps) while the leaves are still moist.

After the desired period, the destruction is determined in %. 100% means that all leafhoppers have been killed; 0% means that none of the leafhoppers have been killed. The kill figures determined form the basis for calculations with Colby's formula.

In this test, a synergistically increased efficacy in comparison with the active compounds when applied individually is shown, for example, by the following active compound combination in accordance with the present application:

TABLE B

| | plant-injurious insects Nephotettix test | |
|---|---|---|
| Active compounds | Active compound concentration in ppm | Percentage destruction after 6 days |
| Ex. (I-b-1) known | 0.32 | 0 |
| Betacyfluthrin known | 0.32 | 50 |
| Ex. (I-b-1) + betacyfluthrin (1:1) according to the invention | 0.32 + 0.32 | found* calc.** $\frac{85 \quad 50}{}$ |

*found = found action
**calc. = action calculated using Colby's formula

Example C

Plutella Test solvent: 7 parts by weight of dimethylformamide
emulsifier: 1 part by weight of alkylaryl polyglycol ether To produce a suitable active compound preparation, 1 part by weight of active compound is mixed with the stated amounts of solvent and emulsifier, and the concentrate is diluted with emulsifier-containing water to the desired concentration.

Cabbage leaves (*Brassica oleracea*) are treated by immersion in the active compound preparation of the desired concentration and are populated with diamond-back moth caterpillars (*Plutella xylostella*) while the leaves are still moist.

After the desired period, the destruction is determined in %. 100% means that all caterpillars have been killed; 0% means that none of the caterpillars have been killed. The kill figures determined are calculated using Colby's formula.

In this test, a synergistically increased efficacy in comparison with the active compounds when applied individually is shown, for example, by the following active compound combination in accordance with the present application:

TABLE C

| | plant-injurious insects Plutella test | |
|---|---|---|
| Active compounds | Active compound concentration in ppm | Percentage destruction after 3 days |
| Ex. (I-b-1) known | 1.6 | 0 |
| Betacyfluthrin known | 1.6 | 80 |
| Ex. (I-b-1) + betacyfluthrin (1:1) according to the invention | 1.6 + 1.6 | found* calc.** $\frac{100 \quad 80}{}$ |

*found = found action
**calc. = action calculated using Colby's formula

Example D

Spodoptera exigua Test solvent: 7 parts by weight of dimethylformamide
emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by immersion in the active compound preparation of the desired concentration and are populated with fall army worm caterpillars (*Spodoptera exigua*) while the leaves are still moist.

After the desired period, the destruction is determined in %. 100% means that all caterpillars have been killed; 0% means that none of the caterpillars have been killed. The kill figures determined are calculated using Colby's formula.

In this test, a synergistically increased efficacy in comparison with the active compounds when applied individually is shown, for example, by the following active compound combination in accordance with the present application:

TABLE D

| | plant-injurious insects Spodoptera exigua test | |
|---|---|---|
| Active compounds | Active compound concentration in ppm | Percentage destruction after 6 days |
| Ex. (I-b-1) known | 8 | 0 |
| Betacyfluthrin known | 8 | 90 |
| Ex. (I-b-1) + betacyfluthrin (1:1) according to the invention | 8 + 8 | found* calc.** $\frac{100 \quad 90}{}$ |

*found = found action
**calc. = action calculated using Colby's formula

Example E

Tetranychus Test (OP-resistant/spray Treatment)

solvent: 7 parts by weight of dimethylformamide
emulsifier: 1 part by weight of alkylaryl polyglycol ether To produce a suitable active compound preparation, 1 part by weight of active compound is mixed with the stated amounts of solvent and emulsifier, and the concentrate is diluted with emulsifier-containing water to the desired concentration.

Bean plants (*Phaseolus vulgaris*) which are severely infested with all stages of the common spider mite (Tetranychus urticae) are sprayed with an active compound preparation of the desired concentration.

After the desired period, the action is determined in %. 100% means that all spider mites have been killed; 0% means that none of the spider mites have been killed. The kill figures determined are calculated using Colby's formula.

In this test, a synergistically increased efficacy in comparison with the active compounds when applied individually is shown, for example, by the following active compound combinations in accordance with the present application:

TABLE E plant-injurious mites
Tetranychus test (OP-resistant/spray treatment)

| Active compounds | Active compound concentration in ppm | Percentage destruction after 14 days |
|---|---|---|
| Ex. (I-b-1) known | 0.32 | 0 |
| Methamidophos known | 0.32 | 0 |
| Ex. (I-b-1) + methamidophos (1:1) according to the invention | 0.32 + 0.32 | found* calc.**<br>90   0 |

*found = found action
**calc. = action calculated using Colby's formula

What is claimed is:

1. A composition comprising a mixture of the compound (I-b-1)

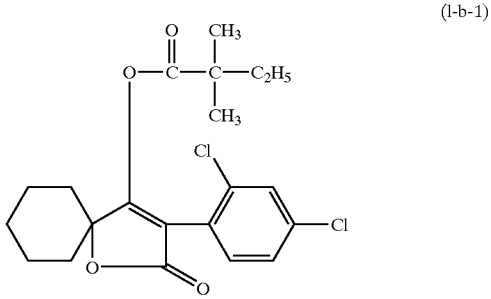

and betacy fluthrin.

2. A method of controlling at least one animal pest comprising applying an insecticidally and/or acaricidally effective amount of the composition of claim 1 to the animal pest and/or its environment.

3. A process for the preparation of an insecticidal and/or acaricidal composition comprising mixing the composition of claim 1 with at least one of extenders and surfactants.

* * * * *